United States Patent [19]

Glazier

[11] Patent Number: 4,883,469
[45] Date of Patent: Nov. 28, 1989

[54] GUARD ASSEMBLY FOR HYPODERMIC NEEDLE

[76] Inventor: Stephen C. Glazier, 211 E. 35th St., Suite 8B, New York, N.Y. 10016

[21] Appl. No.: 179,434

[22] Filed: Apr. 8, 1988

[51] Int. Cl.⁴ .............................................. A61M 5/32
[52] U.S. Cl. ..................................... 604/192; 604/263
[58] Field of Search ......................... 604/192, 263, 187

[56] References Cited

U.S. PATENT DOCUMENTS

| | | | |
|---|---|---|---|
| 2,688,963 | 9/1954 | Smith | 128/216 |
| 3,658,061 | 4/1972 | Hall | 604/263 |
| 3,712,302 | 1/1973 | Burke et al. | 128/221 |
| 4,329,989 | 5/1982 | Dallons et al. | 128/218 |
| 4,623,336 | 11/1986 | Pedicane et al. | 604/192 |
| 4,636,201 | 1/1987 | Ambrose et al. | 604/192 |
| 4,664,259 | 5/1987 | Landis | 206/365 |

OTHER PUBLICATIONS

New York Times, "New Products to Prevent Accidental Needle Sticks", Mar. 27, 1988.
ICU Medical Advertisement, The First Line of Defense Against Needle Stick Injuries.

Primary Examiner—John D. Yasko
Attorney, Agent, or Firm—Harrison & Egbert

[57] ABSTRACT

A guard assembly for a hypodermic needle comprising a hinge guard portion. The hinge is connected to the hypodermic needle at a location distal the pointed end of the needle. The guard portion is attached to the hinge such that the guard portion is movable relative to the needle. The guard portion has a receiving slot extending longitudinally therethrough for receiving the pointed end of a hypodermic needle. The receiving slot opens through the wall transverse to the longitudinal axis of the guard portion. The hinge is a flexible strip connected at one end to the needle and at the other end at the guard portion. The guard portion is a cylindrical member having a longitudinal V-cut narrowing from the wall of the cylindrical member to the receiving slot. An end cap is fixed to the end of the cylindrical member so as to cover the end of the longitudinal V-cut and receiving slot. The hinge may include a sheath portion with an inner area attached to the exterior of the hypodermic needle.

16 Claims, 6 Drawing Sheets

GUARD ASSEMBLY FOR HYPODERMIC NEEDLE

TECHNICAL FIELD

The present invention relates to guard assemblies for hypodermic needles. More particularly, the present invention relates to syringes, catheters, and related devices, for the prevention of accidental needle stick injuries after use and prior to disposal.

BACKGROUND ART

Hypodermic needles are in common use today on syringes, catheters, and related devices. They are used for subcutaneous injection, the taking of blood samples, the intravenous administration of medicines, biopsies, and other medical procedures. The needles are usually supplied in sterilized individual packages and are meant to be used once and then disposed of, although some needles are meant to be re-used after sterilization. A single use of a hypodermic needle renders it non-sterile and septic, and potentially contaminated by blood-borne diseases which may be present in the patient. Such contamination can include AIDS, hepatitis, venereal disease, and other blood-borne diseases.

A hypodermic needle has a sharp end for the purpose of better penetrating the human body. A major source of injury and infection to health care workers has been the accidental sticks and jabs by septic, used hypodermic needles. Before their disposal or re-sterilization, the accidental penetration of the body by these jabs causes a deep puncture wound. A stab by a needle that has been used in an infected patient can spread the patient's infection to the health care worker. The major cause of the spread of the AIDS epidemic and the hepatitis epidemic to health care workers has been the accidental stabs of these workers by previously used, contaminated needles.

This problem is often aggravated by the fact that disposal of medical debris is often made in modern plastic garbage bags. These garbage bags are easily punctured by the disposable, contaminated hypodermic needle. Accidental stabbings can occur to the maintenance personnel or other personnel involved in the disposal of medical refuse.

In the case of sterilization, reusable needles, accidental stabbings can occur between prior use and later sterilization.

Some attention has been given to developing guards for hypodermic needles to protect from accidental needle stabs. U.S. Pat. No. 3,688,936, to Smith, and U.S. Pat. No. 3,612,302, to Burke and Raines, show needles with caps over them. Although the caps, once in place, will protect from needle stabs, the act of placing the caps over the needles places the fingers holding the cap in front of the tip of the needle. While inserting the tip of the needle into the cap, a "near miss" can stab the fingers holding the cap. Capping the needle may place the health care worker in more danger of accidental needle stabs than if the needle were disposed of without a cap at all.

U.S. Pat. No. 4,329,989, issued to Dallons et al., shows a cap attached to the needle assembly. This provides for convenience in preventing the misplacement of the cap, but does nothing to keep the fingers from being in front of the needle tip when applying the cap. Once again, this patent shows a misconception in the past. This misconception is that needle jabs will be prevented by placing a cap over the end of the needle. In actuality, many of these accidental stabbings occur during the process of placing such a safety cap over the hypodermic needle.

U.S. Pat. No. 4,623,336, issued to Pedicano et al., shows a needle guard cap that requires that fingers to be in front of the tip of the needle to apply the cap, but the cap has a large flange guard to protect the fingers when inserting the needle into the cap. Unfortunately, the resulting cap is large, cumbersome, relatively expensive, and is not part of an integrated needle assembly. This cap is not in common use in the medical profession.

A device for the prevention of accidental needle stick injuries has been developed and introduced by ICU Medical, Inc. of Mission Viejo, Calif. This device is a pop-up needle guard. This guard has an open end that allows the health care worker to inject the patient with the needle. Unfortunately, this open end can "pop-down" or "pop-off" to expose the tip of the needle, after the guard is "popped-up" following injection. Simple inadvertent wiggling manipulation of the device can cause this inadvertent "pop-down" or "pop-off". This wiggling is facilitated by the fact that the diameter of the guard must be larger than that of the needle, especially at the open end of the guard. Also, a simple hard jamming motion on the tip of the guard after it is "popped-up" can cause it to "pop-down", exposing the needle. Also, this needle-guard assembly must have two moving parts assembled together. The snap-lock portion requires precise engineering, manufacture and assembly. This is an extremely costly feature in relation to the cost of the hypodermic needle itself, and deters wide-spread use.

It is an object of the present invention to provide a guard for hypodermic needles to prevent accidental needle stab injuries by previously used, septic, hypodermic needles.

It is another object of the present invention to prevent puncture wounds and the spread of infectious disease to health care workers and others.

It is still another object of the present invention to provide such a guard that can be inserted over a used needle without requiring the fingers of the health care worker to be placed in front of the tip of the needle.

It is another object of the present invention to provide such a guard with a closed end over the tip of the needle so that an accidental jabbing motion will not cause the guard to "pop-down" and again expose the top of the needle.

It is a further object of the present invention to provide such a guard assembly as a part of an integrated needle assembly capable of inexpensive manufacture, compact size, convenient use, and reliability.

It is still another object of the present invention to provide a means by which a hospital or other health care facility can accommodate the desires of its medical service personnel to reduce the risk to them of injury from needle stabs and infection by AIDS and other blood-borne diseases.

These and other objects and advantages of the present invention will become apparent from a reading of the attached specification and appended claims.

SUMMARY OF THE INVENTION

The present invention is a hypodermic needle and needle guard assembly that can be attached to a syringe, catheter, or similar device or installed during manufacture as an integral part of such device. The present invention is intended to be disposed of after one use, or to be sterilized and reused after each use.

The present invention is a guard assembly for a hypodermic needle that comprises a hinge extending from a central portion of the needle, and a guard portion attached to the hinge. The guard portion is movable relative to the needle. The guard has a receiving slot that extends longitudinally through the guard for receiving the pointed end of the hypodermic needle. The receiving slot opens through the wall of the guard transverse the longitudinal axis of the guard. This slot receives the pointed end of the hypodermic needle. The hinge may be connected directly to the needle, may be attached to a fixed ring surrounding the needle, or attached to a sheath surrounding a portion of the needle.

The hinge is flexible strip attached to a central portion of the needle at one end and at the other end to the guard portion. The hinge is suitable for allowing the guard to rotate relative to the needle.

The guard portion is a cylindrical member having a longitudinal V-cut narrowing from the wall of the guard member to the receiving slot. An end cap is fitted to the end of the cylindrical member and covers the end of the longitudinal V-cut and the receiving slot. Alternatively, the receiving slot and V-cut can be formed within the cylindrical member for less than the entire length of the guard portion. A locking mechanism is formed within the guard portion for retaining the hypodermic needle within the retaining slot.

A fastener is attached to the exterior of the needle. This fastener is suitable for detachably fixing the guard in a rotated position distal the pointed end of the hypodermic needle.

The assembly is manufactured such that the assembly may be attached to the syringe by the traditional attachment means. A detachable cap surrounds the assembly until the syringe is prepared for use. The syringe is then used with the guard portion attached distal the pointed end of the needle. After the use of the needle, the guard can be detached from the needle, while the hinge remains attached to the needle, and the guard folded across the hinge such that the exposed portion of the needle inserts into the length of the slot within the guard portion. The pointed end of the needle is then trapped in the bottom of the guard slot and is covered by the guard.

The assembly may also include a sheath over the needle portion between the attachment of the hinge to the needle and the attachment of the needle to the syringe, including the detachable fastener for the guard. The sheath portion is a plastic tubular section having an inner diameter corresponding to the outer diameter of the hypodermic needle. The flexible plastic strip/hinge has one end connected to the sheath and the other end connected to the guard.

DETAILED DESCRIPTION OF THE INVENTION

Figure 1:
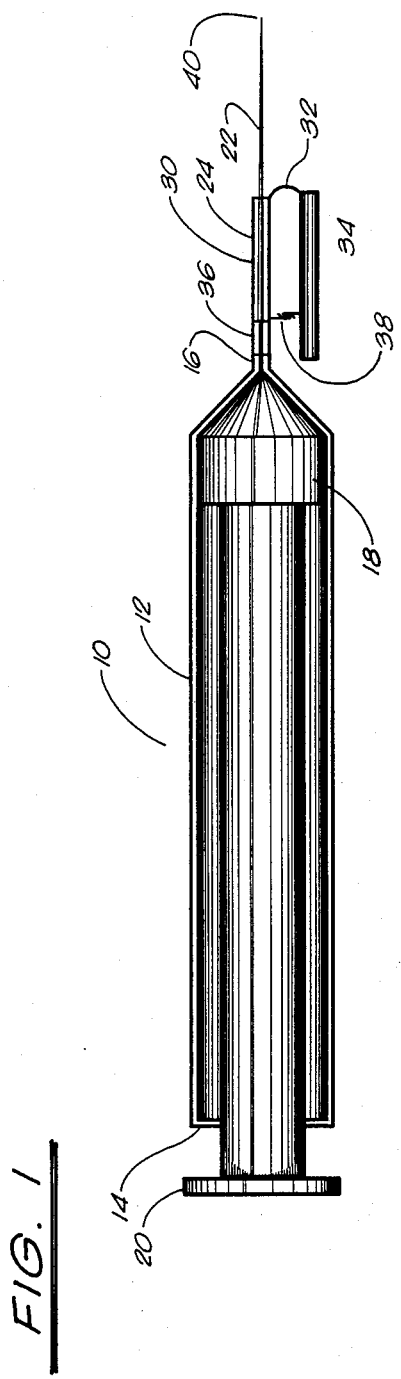
FIG. 1 is a cross-sectional view, in side elevation, of the syringe having the guard assembly attached and in its pre-use position.

Referring to FIG. 1, there is shown at 10, a syringe in accordance with the preferred embodiment of the present invention. Syringe 10 includes a barrel 12 having one open end 14 and one closed end 16, a piston 18 slidably positioned within barrel 12, a shaft 20 extending beyond the open end 14 of barrel 12, a hypodermic needle 22 connected to and communicating with the restricted end 16 of barrel 12, and a guard assembly 24 fastened to the hypodermic needle 22. The principal feature of the present invention is the arrangement and configuration of guard assembly 24, alone and in combination with syringe 10.

Generally, syringe 10 is a standard, commercially available syringe. The piston 18 forms a liquid-tight seal with the interior of barrel 12. Shaft 20 extends beyond the open end 14 of barrel 12 and acts as a plunger relative to the piston 18. The hypodermic needle 22 is attached to the restricted end 16 of barrel 12 through standard means, such as a luer lock. It should be noted that the guard assembly 24 can used in combination with a standard syringe, as shown in FIG. 1, or with various types of syringes. In particular, the present invention can be used in combination with a non-reusable syringe of a type identified in U.S. Pat. No. 4,699,614, issued on Oct. 13, 1987, to the present inventor.

In FIG. 1, guard assembly 24 can be seen as having a sheath portion 30, a hinge 32, and a guard portion 34. The sheath 30 has an inner area suitable for attachment to the exterior of hypodermic needle 22. The hinge 22 extends from one end of sheath 30 and is attached to an end of guard portion 34. The guard 34 is movable with respect to the sheath portion. The sheath 30 may be directly affixed to the exterior of hypodermic needle 22 or may be connected to the restricted end 16 of barrel 12 by way of a luer lock 36. The sheath portion 30 is a plastic tube that has an inner diameter generally matching the outer diameter of the hypodermic needle 22. The sheath 30 covers approximately half of the length of the hypodermic needle 22. One end of the sheath 30 is juxtaposed against the restricted end 16 of barrel 12.

It should be noted here that the use of sheath portion 30 is only considered as part of the "best mode" of the present invention. There are a number of alternative modes to that of the use of sheath portion 30. The hinge 32 could have one end attached directly to the exterior of the hypodermic needle 22 or to the exterior of the hypodermic needle 22 or to the exterior of the syringe 10. Instead of a sheath portion, the hinge could be connected to a thin ring extending around the hypodermic needle. The present invention should not be limited by the particular manner of connecting the hinge to the hypodermic needle.

Hinge 32 is connected between the sheath portion 30 and the guard portion 34. Hinge 32 allows rotational movement of the guard portion 34 relative to the sheath portion 30. The hinge 32 is a flexible strip of plastic that has one end attached to the end of sheath 30 and the other end attached to the end of guard portion 34.

A fastener 38 is attached to the exterior of sheath 30. Fastener 38 is suitable for detachably receiving the guard portion 38 in a position distal from the pointed end 40 of hypodermic needle 22, as shown in FIG. 1. This fastener 38 can have a variety of configurations. Fastener 38 can be a small piece of VELCRO, a plastic button/hole configuration, a meshing teeth configuration, or a variety of other arrangements. The important aspect of fastener 38 is that it maintain guard portion 34 in a position removed from the forward portion 40 of hypodermic needle 22. As can be seen in FIG. 1, fastener 38 has one portion extending downwardly from the sheath 30 and another portion attached to the guard 34. It is preferable that a simple manipulation be sufficient to allow the guard 34 to disengage from the fastener 38 and the sheath 30.

Figure 2:
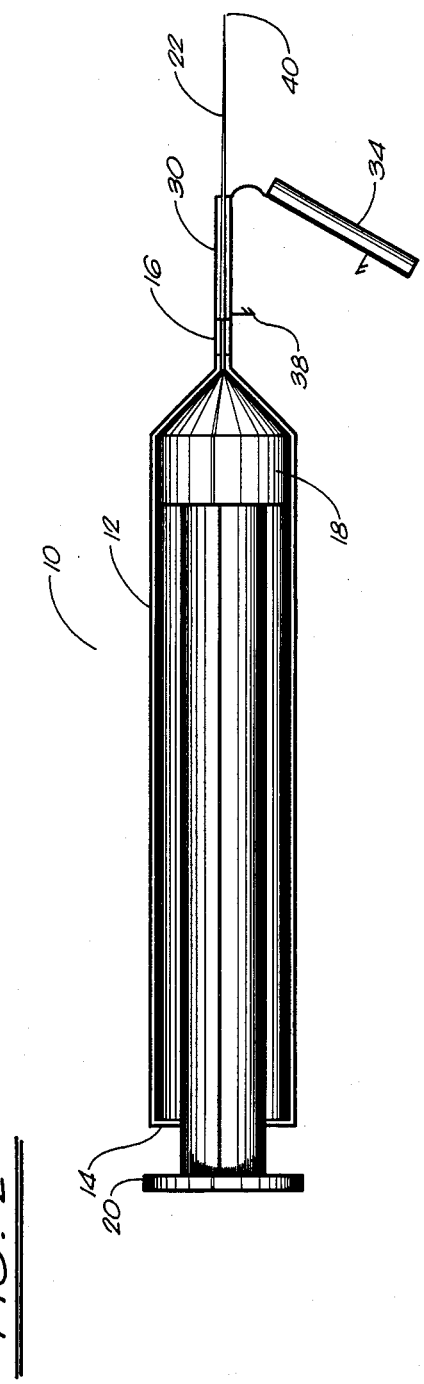
FIG. 2 is a view, similar to FIG. 1, showing the rotation motion of the guard portion relative to the sheath portion of the guard assembly.

FIG. 2 shows the second step in the utilization of the present invention. In FIG. 2, the syringe 10 has been used on a patient. At the point in time illustrated in FIG. 2, the tip 40 of hypodermic needle 22 has been contaminated by the blood of a patient. Following use, the operator of the syringe 10 pushes the guard 34 downwardly so as to detach guard 34 from fastener 38. As can be seen, guard 34 begins a rotation away from the restricted end of barrel 12 toward the end 40 of hypodermic needle 22. During this motion, the operator of the syringe 10 is pushing guard portion 34 from the rear. At no time does the operator exert any motion forward of the end 40 of hypodermic needle 22.

Figure 3:
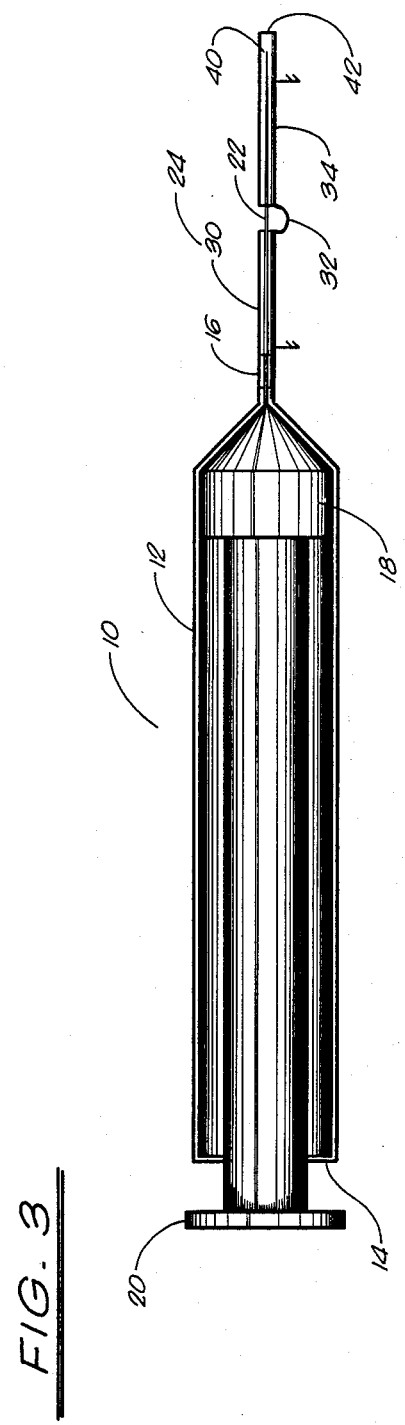
FIG. 3 shows the guard assembly as arranged in its proper position following use of the hypodermic needle.

FIG. 3 shows the guard assembly 24 in its proper configuration after usage of hypodermic needle 22. As can be seen, the guard portion 34 has been fully rotated so as to receive the end 40 of hypodermic needle 22. The hinge 32 allows this complete rotation to occur. As can be seen in FIG. 3, the tip 40 of hypodermic needle 22 is positioned well back of the end 42 of the guard portion 34. The sheath portion 30 remains in a locked position around hypodermic needle 22. In the position illustrated in FIG. 3, it is impossible for one having an inadvertent encounter with the syringe 10, to be stabbed by the end 40 of the syringe. The guard portion 34 firmly locks about the hypodermic needle 22 so as to prevent accidental stabbing. The plastic used in the manufacture of guard portion 34 should be of a quality such that the tip 40 will not easily penetrate through the plastic to the end 42 of guard portion 34.

Figure 4:
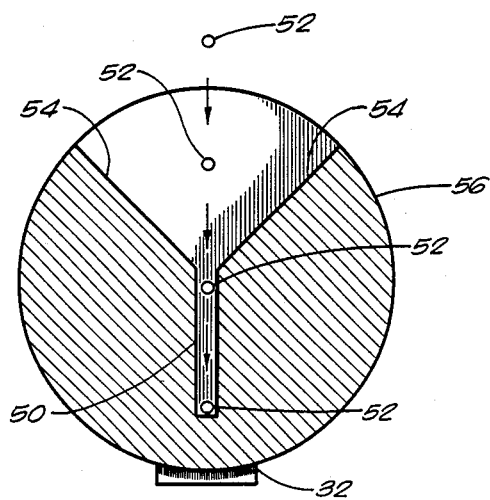
FIG. 4 is a cross-sectional end view of the guard assembly of the present invention.

FIG. 4 is a cross-sectional view of the guard portion 34. It can be seen that the guard portion 34 has a receiving slot 50 extending longitudinally through the guard portion 34. The small circles 52, shown in FIG. 4 show the direction of travel of the hypodermic needle 22 into this receiving slot 50 of guard 34. The receiving slot 50 opens through the wall of the guard portion 34 transverse to the longitudinal axis of the guard portion. It can be seen that guard portion 34 is a cylindrical member having a V-cut 54 narrowing from the wall 56 to the receiving slot 50. The V-cut serves to properly funnel the needle 52 into the receiving slot 50. Hinge is fastened to the bottom of the wall 56 of the guard portion 34.

Figure 5:
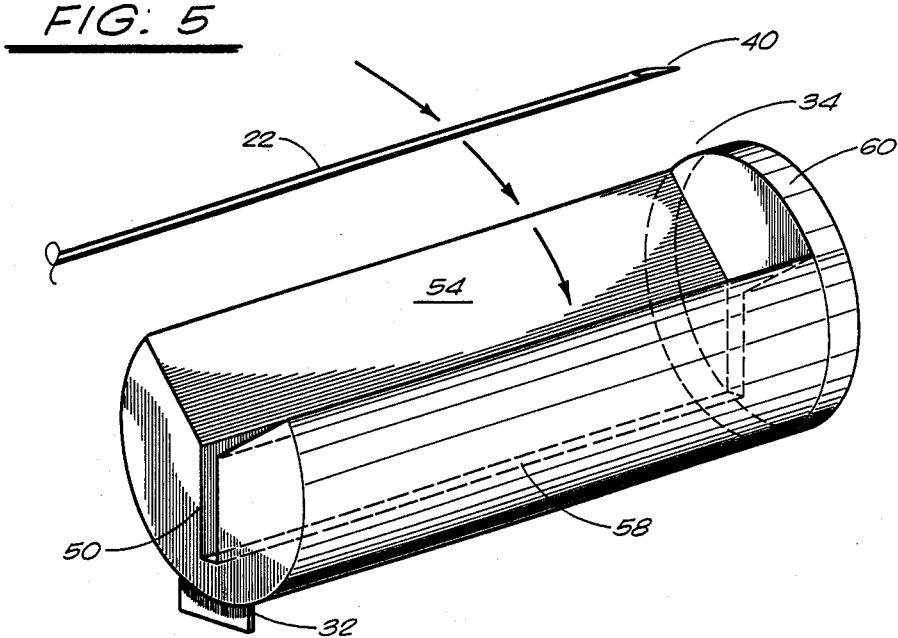
FIG. 5 is a perspective view of the guard portion showing the motion of the hypodermic needle into the guard portion.

FIG. 5 shows, in perspective, the use of guard portion 34. It can be seen that the guard portion 34, when rotated about hinge 32 moves so as to intercept hypodermic needle 22. The V-cut walls 54 cause the hypodermic needle 22 to funnel toward the receiving slot 50. In its final position, the hypodermic needle 22 will rest adjacent the bottom 58 of receiving slot 50.

FIG. 5 shows an end cap 60 fixed to the end of the cylindrical guard portion 34. End cap 60 has a discoidal shape and covers the end of the longitudinal V-cut 54 and the receiving slot 50. When the hypodermic needle 22 is in its position at the bottom 58 of slot 50, the end 40 will generally abut the inner side of end cap 60.

Importantly, and alternatively, end cap 60 can be integral with the guard portion 34. In this configuration, the guard portion 34 and the end cap 60 are molded from the same form. As a result, the longitudinal V-cut 54 and the receiving slot 50 extend for less than the entire length of the guard portion 34.

Figure 6:
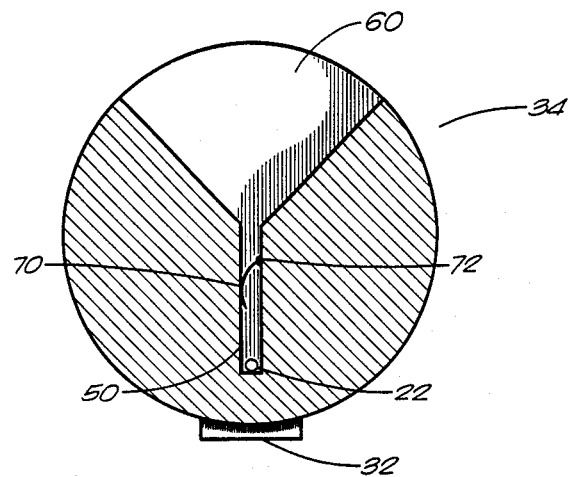
FIG. 6 is an end view of the guard portion as seen from the hinge showing, in particular, one embodiment of the locking arrangement.

FIG. 6 shows the arrangement for locking the hypodermic needle 22 within the receiving slot 50. The embodiment shown in FIG. 6 includes a one-way flap 70. One-way flap 70 is a strip of material fastened at point 72 along one wall of the slot 50. The flap 70 has a curvature that allows the hypodermic needle 22 to pass inwardly past flap 70. However, once the hypodermic needle 22 passes by flap 70, the hypodermic needle 22 cannot pass from the slot without the removal of flap 70.

Figure 7:
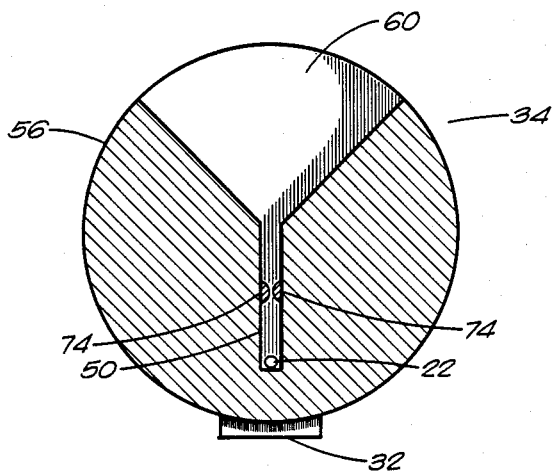
FIG. 7 is an end view showing an alternative locking arrangement.

FIG. 7 shows an alternative technique for trapping the hypodermic needle 22 within slot 50. In the configuration of FIG. 7, a pair of bumps 74 are formed so as to extend outwardly from the walls of slot 50. The distance between the bumps 74 should be less than the width of the hypodermic needle 22. Hypodermic needle 22 passes between these bumps 74 by pressing on the wall 56 of the guard portion 34. During entry, the slot 50 will deform slightly under pressure so as to permit the admission of hypodermic needle 22 between bumps 74. Hypodermic needle 22 will not pass from the slot 50 unless a greater pressure is exerted on the opposite side of the wall 56.

Figure 8:
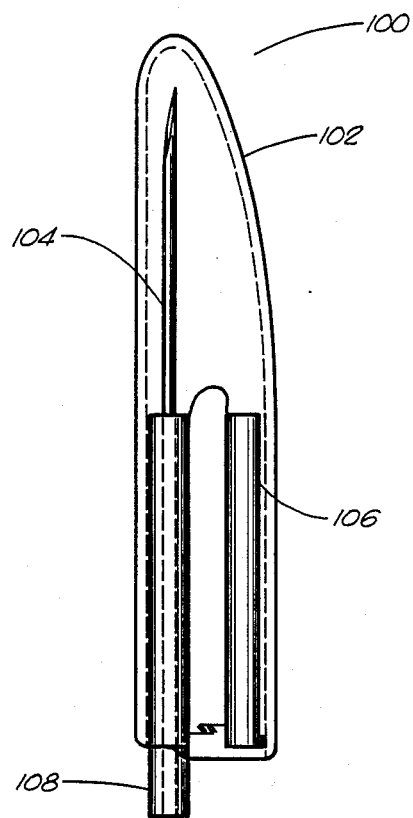
FIG. 8 is a side elevational view showing the entire needle/needle guard assembly of the present invention, prior to attachment, with a removable protective cap attached thereto.

FIG. 8 shows the configuration of the present invention in a form suitable for distribution. In many circumstances, the syringe is shipped separate from the hypodermic needle. FIG. 8 show such an arrangement 100 in proper condition for shipment. It can be seen that the entire needle/needle guard assembly 100 is provided with a protective removable cap 102. Removable cap 102 surrounds the hypodermic needle 104 and the guard assembly 106. The removable cap 102 has an inner diameter that is greater than the cross-section of the guard assembly 106 when the guard assembly is in its retracted position. The attachment section 108 extends outwardly from protective cap 102 so as to allow the assembly to be properly attached to a syringe. Following the connection of attachment section 108 to a syringe and prior to use, the protective cap 102 is detached from around the guard assembly 106. Following use and injection, the guard assembly is positioned in the manner illustrated in FIG. 3. While in this protective position, the cap 102 can be reattached over the guard assembly. THe protective cap 102 can, thus be reattached without the risk of a health worker's fingers being stabbed by the hypodermic needle 104.

The present invention can be disposed of, or await cleaning and sterilization prior to reuse, in the configuration indicated in FIG. 3, with or without the protective cap 102.

The present invention provides a protective cover over the sharp end of the hypodermic needle. The guard used to cover the end of the hypodermic needle will servo to prevent accidental needle stab injuries, puncture wounds, and the spread of infectious disease to health care workers and others. The guard mechanism of the present invention can be utilized without requiring the fingers of the health care worker to be placed in front of the tip of the needle. As a result, there is little risk of an accidental needle stab. The present invention can also be manufactured, implemented, and utilized for a relatively minimal cost. In the hospital industry, costs are an important factor and, as a result, the present invention would be more likely to be utilized than those of greater expense. Since the present invention is of benefit in the prevention of the spread of disease, the present invention will be available as an attractive alternative to more expensive techniques for the prevention of needle stabs.

The embodiments as illustrated and discussed in this specification are intended only to teach those skilled in the art the best way known by the inventor to make and use the invention. Nothing in the specification should be considered as limiting the scope of the present invention. The present invention should only be limited by the following claims and their legal equivalents.

I claim:

1. The guard assembly for a hypodermic needle comprising:
    a hinge means connected to said hypodermic needle at a location distal the pointed end of said hypodermic needle; and
    guard means attached to said hinge means such that said guard means is movable relative to said hypodermic needle, said guard means having a receiving slot extending longitudinally through at least a portion of said guard means, said receiving slot opening through the wall transverse to the longitudinal axis of said guard means, said guard means for receiving the pointed end of said hypodermic needle, said guard means comprising:
    a cylindrical member having a longitudinal V-cut narrowing from the wall to said receiving slot;
    an end cap fixed to the end of said cylindrical member, said end cap covering the end of said longitudinal V-cut and said receiving slot; and
    lock means formed within said receiving slot for retaining said hypodermic needle within said receiving slot.

2. The assembly of claim 1, said hinge means comprising:
    a sheath portion having an inner area suitable for attachment to the exterior of a hypodermic needle.

3. The assembly of claim 2, said sheath portion comprising:
    attachment means connected to said sheath portion for locking said sheath portion to the end of said hypodermic needle opposite said pointed end of said hypodermic needle.

4. The assembly of claim 2, said sheath portion being a plastic tubular section having an inner diameter corresponding to the outer diameter of said hypodermic needle.

5. The assembly of claim 1, hinge means comprising a flexible strip attached at one end to said hypodermic needle and at the other end to said guard means.

6. The assembly of claim 2, said hinge means suitable for allowing said guard means to rotate relative to said sheath portion.

7. The assembly of claim 1, said hinge means further comprising:
    a fastener attached to the exterior of said hypodermic needle, said fastener suitable for detachably fixing said guard means in a position distal the pointed end of said hypodermic needle.

8. A syringe comprising:
    a barrel having one opened and one restricted end through which a liquid may pass;
    a piston slidably positioned within said barrel, said piston forming a liquid-tight seal with the interior of said barrel;
    a shaft extending beyond said open end of the said barrel and connected to said piston;
    a hypodermic needle connected to and communicating with said restricted end of said barrel; and
    a guard assembly fastened to said hypodermic needle and having a guard portion generally rotatably connected thereto, said guard portion movable between a first position adjacent the end of said hypodermic needle attached to said restricted end of said barrel and a second position covering the other end of said hypodermic needle; said guard assembly comprising:
    a sheath portion in fixed attachment to the end of said hypodermic needle adjacent the restricted end of said barrel, said guard portion rotatably connected to said sheath portion, said guard portion having a receiving slot extending longitudinally through said guard portion for receiving the pointed end of said hypodermic needle, said guard portion comprising a cylindrical member having a longitudinal V-cut extending for less than the entire length of said cylindrical member, said V-cut narrowing to and communicating with said receiving slot, said receiving slot having a length corresponding to the length of said V-cut, said guard portion having an end cap at the end opposite said sheath portion, said end cap covering the pointed end of said hypodermic needle.

9. The syringe of claim 8, said sheath portion comprising a plastic tube having an inner diameter corresponding to the outer diameter of said hypodermic needle.

10. The syringe of claim 9, said sheath portion covering less than the entire length of said hypodermic needle, said sheath portion having one end generally juxtaposed again the restricted end of said barrel.

11. The syringe of claim 8, said guard assembly further comprising:
    a hinge connected to said hypodermic needle and said guard portion, said hinge allowing rotational movement of said guard portion relative to said hypodermic needle.

12. The syringe of claim 11, said hinge comprising a flexible strip having one end attached to said needle and the other end attached to said guard portion.

13. The syringe of claim 8, said guard portion comprising:
    lock means formed within said receiving slot for retaining said hypodermic needle in said receiving slot.

14. The syringe of claim 8, said guard assembly further comprising:

fastening means connected to the exterior of said sheath portion, said fastening means for detachably maintaining said guard portion in a position removed from the pointed end of said hypodermic needle.

15. The syringe of claim 8, further comprising:
a removable cap surrounding said hypodermic needle and said guard assembly, said removable cap having an inner diameter greater than the cross-section of said guard assembly with said guard portion in said first position.

16. The syringe of claim 1, said guard assembly further comprising:
a removable cap surrounding said hypodermic needle, said hinge means, and said guard means, said removable cap having an inner diameter greater than the cross-section of said guard means and said hinge means.

* * * * *